US012016846B2

(12) United States Patent
Friedlander et al.

(10) Patent No.: US 12,016,846 B2
(45) Date of Patent: Jun. 25, 2024

(54) METHODS OF TREATING ANEURYSMS

(71) Applicants: UNIVERSITY OF PITTSBURGH—OF THE COMMONWEALTH SYSTEM OF HIGHER EDUCATION, Pittsburgh, PA (US); UPMC, Pittsburgh, PA (US)

(72) Inventors: Robert Max Friedlander, Pittsburgh, PA (US); Wendy Fellows Mayle, Mingo Junction, OH (US); Michael P. D'Angelo, New York, NY (US); Kamil W. Nowicki, Pittsburgh, PA (US)

(73) Assignees: UNIVERSITY OF PITTSBURGH—OF THE COMMONWEALTH SYSTEM OF HIGHER EDUCATION, Pittsburgh, PA (US); UPMC, Pittsburgh, PA (US)

( * ) Notice: Subject to any disclaimer, the term of this patent is extended or adjusted under 35 U.S.C. 154(b) by 0 days.

(21) Appl. No.: 17/404,395

(22) Filed: Aug. 17, 2021

(65) Prior Publication Data
US 2022/0054463 A1 Feb. 24, 2022

Related U.S. Application Data

(60) Provisional application No. 63/067,604, filed on Aug. 19, 2020.

(51) Int. Cl.
*A61K 31/4365* (2006.01)
*A61K 31/18* (2006.01)
*A61P 9/14* (2006.01)
*C07K 16/28* (2006.01)

(52) U.S. Cl.
CPC .......... *A61K 31/4365* (2013.01); *A61K 31/18* (2013.01); *A61P 9/14* (2018.01); *C07K 16/2866* (2013.01)

(58) Field of Classification Search
CPC ....... A61K 31/4365; A61K 31/18; A61P 9/14; C07K 16/2866
See application file for complete search history.

(56) References Cited

FOREIGN PATENT DOCUMENTS

WO WO 2011/100271 A2 8/2011
WO WO 2014/184384 A1 11/2014

OTHER PUBLICATIONS

Matsumoto et al., 12(1) Drugs Rd, 1-7 (2012) (Year: 2012).*
Aldi, "The CRISPR tool kit for genome editing and beyond," Nat Communications, 9:1911 (2018).
Bownstein et al., "Genes Associated with Thoracic Aortic Aneurysm and Dissection: An Update and Clinincal Implications," AORTA (Stamford) 5(1): 11-20 (2017).
Brummelkamp, "A System for Stable Expression of Short Interfering RNAs in Mammalian Cells," Science 296: 550-553 (2002).
Calero et al., "Overview of aortic aneurysm management in the endovascular era," Semin Vasc Surg., 29(1-2):3-17 (2016).
Elbashir et al., "Duplexes of 21-nucleotide RNAs mediate RNA interference in cultures mammalian cells," Nature 411:494-498 (2001).
Haseloff et al., "Simple RNA enzymes with new highly specific endoribonuclease activities," Nature, 334:585 (1988).
Hosaka et al., "Modified murine intracranial aneurysm model: aneurysm formation and rupture by elastase and hypertension," Journal of neurointerventional surgery, 6:474-479 (2014).
Huesken et al., "Design of a genome-wide siRNA library using an artificial neural network," Nat. Biotechnol. 23, 995-1001 (2005).
Jagla et al., "Sequence characteristics of functional siRNAs," RNA 11:864-872 (2005).
Kim et al., "Three-dimensional model of the active site of the self-splicing rRNA precursor of *Tetrahymena*," Proc Natl Acad Sci USA, 84:8788 (1987).
Lee et al., "Expression of small interfering RNAs targeted against HIV-1 rev transcripts in human cells," Nature Biotechnol., 20:500-505 (2002).
Maeder et al., "Genome-editing Technologies for Gene and Cell Therapy," Mol Ther., 24(3):430-446 (2016).
Shabalina et al., "Computational models with thermodynamic and composition features improve siRNA design," BMC Bioinformatics 7:65, 16 pages (2006).
Weintraub, "Understanding Abdominal Aortic Aneurysm," N Engl J Med., 361(11): 1114-1116 (2009).
Aldi et al., "The CRISPR tool kit for genome editing and beyond," Nat Commun. 9:1911 (2018).
Brownstein et al., Genes Associated with Thoracic Aortic Aneurysm and Dissection, AORTA 5(1):11-20 (2017).
Calero et al., "Overview of aortic aneurysm management in the endovascular era," Semin Vasc Surg. 29:3-17 (2016).
Elbashir et al., "Duplexes of 21±nucleotide RNAs mediate RNA interference in cultured mammalian cells," Nature 411:494-498 (2001).
Haseloff et al., "Simple RNA enzymes with new and highly specific endoribonulcease activities," Nature 334:585-591 (1988).
Huesken et al., "Design of a genome-side siRNA library using an artificial neural network," Nat. Biotechnol. 23(8):995-1001 (2005).
Jeffries et al., "A catalytic 13-mer ribozyme," Nucleic Acid Res, 17(4): 1371-1377 (1989).
Kim et al., "Three-dimensional model of the active site of the self-splicing rRNA precursor of Tetrahymena," Proc Natl. Acad Sci USA, 84:8788-8792 (1987).
Lee et al., "Expression of small interfering RNAs targeted against HIV-1 rev transcripts in human cells," Nature Biotechnol. 19:500-505 (2002).
Shabalina et al., "Computational models with thermodynamic and composition features improve siRNA design," BMC Bioinformatics 7:65 (2005) 16 pgs.

* cited by examiner

*Primary Examiner* — Timothy R Rozof
(74) *Attorney, Agent, or Firm* — Baker Botts L.L.P.

(57) ABSTRACT

The present disclosure relates to the use of a platelet inhibitor to prevent and/or treat aneurysms. The methods include prevention and/or treatment of aneurysms with the administration of a platelet inhibitor to a subject. The present disclosure further provides kits for performing such methods.

8 Claims, 11 Drawing Sheets
(6 of 11 Drawing Sheet(s) Filed in Color)

Human        Mouse        Human EM

Continued on FIG. 5 continued

METHODS OF TREATING ANEURYSMS

CROSS-REFERENCE TO RELATED APPLICATIONS

This application is a U.S. Patent Application which claims priority to U.S. Provisional Patent Application Ser. No. 63/067,604, filed on Aug. 19, 2020, the contents of each of which are incorporated by reference herein in their entirety.

FIELD OF INVENTION

The present disclosure relates to the use of platelet inhibitors to prevent and/or treat aneurysms.

BACKGROUND

Cerebral aneurysms are focal dilations of cerebral arteries that are present in 3-5% of the general population. Almost 95% of these vascular lesions are sporadic, while the remaining 5% can be attributed to familial, infectious or traumatic causes. These lesions can rupture resulting in subarachnoid hemorrhage leading to near 50% mortality and morbidity. Despite numerous studies, the true cause of why cerebral aneurysms form is still not well understood. There are currently no medical therapies available, and cerebral aneurysms are managed via open surgical procedures, endovascular surgery, or a combination of the two approaches. It is thought that cerebral aneurysms are sporadic lesions caused by a combined effect of inflammation and hemodynamic stress. However, standard anti-inflammatory agents are not routinely used due to increased risk of hemorrhage.

Accordingly, there remains a need in the art for novel agents in the treatment of aneurysms and cerebral aneurysms.

SUMMARY

The present disclosure provides methods and compositions for treating aneurysms in a subject. In one aspect, the present disclosure provides a method for treating an aneurysm in a subject in need thereof, comprising administering a therapeutically effective amount of a platelet inhibitor to the subject. In certain embodiments, the platelet inhibitor is administered orally.

In certain embodiments, the platelet inhibitor is selected from the group consisting of a glycoprotein IM/IIIA inhibitor, a CXCL7 inhibitor, a CXCR1/2 inhibitor, and a combination thereof. In certain embodiments, the platelet inhibitor is a glycoprotein IIB/IIIA inhibitor. In certain embodiments, the glycoprotein IM/IIIA inhibitor is clopidogrel, a salt thereof, or a derivative thereof. In certain embodiments, the platelet inhibitor is a CXCL7 inhibitor. In certain embodiments, the CXCL7 inhibitor is an antibody anti-CXCL7. In certain embodiments, the platelet inhibitor is a CXCR1/2 inhibitor. In certain embodiments, the CXCR1/2 inhibitor is reparixin, a salt thereof, or a derivative thereof.

In certain embodiments, the aneurysm is an abdominal aortic aneurysm. In certain embodiments, the aneurysm is a thoracic aortic aneurysm. In certain embodiments, the aneurysm is a cerebral aneurysm.

In certain embodiments, the method further comprises administering a therapeutically effective amount of a secondary aneurysm inhibitor. In certain embodiments, the platelet inhibitor is administered to the subject at a dose from about 0.05 mg/kg to about 100 mg/kg. In certain embodiments, the administration of the platelet inhibitor reduces the development, growth and/or rupture of the aneurysm.

In one aspect, the present disclosure provides a method for preventing or reducing the risk of growth and/or rupture of an aneurysm in a subject in need thereof, comprising administering a therapeutically effective amount of a platelet inhibitor to the subject. In certain embodiments, the platelet inhibitor is administered orally.

In certain embodiments, the platelet inhibitor is selected from the group consisting of a glycoprotein IM/IIIA inhibitor, a CXCL7 inhibitor, a CXCR1/2 inhibitor, and a combination thereof. In certain embodiments, the platelet inhibitor is a glycoprotein IIB/IIIA inhibitor. In certain embodiments, the glycoprotein IM/IIIA inhibitor is clopidogrel, a salt thereof, or a derivative thereof. In certain embodiments, the platelet inhibitor is a CXCL7 inhibitor. In certain embodiments, the CXCL7 inhibitor is an antibody anti-CXCL7. In certain embodiments, the platelet inhibitor is a CXCR1/2 inhibitor. In certain embodiments, the CXCR1/2 inhibitor is reparixin, a salt thereof, or a derivative thereof.

In certain embodiments, the aneurysm is an abdominal aortic aneurysm. In certain embodiments, the aneurysm is a thoracic aortic aneurysm. In certain embodiments, the aneurysm is a cerebral aneurysm.

In certain embodiments, the method further comprises administering a therapeutically effective amount of a secondary aneurysm inhibitor. In certain embodiments, the platelet inhibitor is administered to the subject at a dose from about 0.05 mg/kg to about 100 mg/kg. In certain embodiments, the administration of the platelet inhibitor reduces the development, growth and/or rupture of the aneurysm.

In one aspect, the present disclosure provides a kit for treating and/or preventing an aneurysm in a subject, comprising a platelet inhibitor. In certain embodiments, the platelet inhibitor is clopidogrel, reparixin, or a combination thereof.

BRIEF DESCRIPTION OF THE DRAWINGS

For a more complete understanding of the present disclosure and its features and advantages, reference is now made to the following description, taken in conjunction with the accompanying drawings. The patent or application file contains at least one drawing executed in color. Copies of this patent or patent application publication with color drawing(s) will be provided by the Office upon request and payment of the necessary fee.

FIG. 1B shows cytokines levels in peripheral intravenous blood and in aneurysm dome tissue.

FIG. 2A shows endothelial cells (CD31+) in human aneurysm tissues from three different patients with positive staining for IL-8 as compared to control superficial temporal arteries.

FIG. 2B shows endothelial cells (CD31+) in human aneurysm tissues from three different patients with positive staining for GRO-α/CXCL1. Scalebar=10 μm.

FIG. 3A shows mice treated with 1 mg/kg clopidogrel developing significantly less aneurysms (0% vs 59%, p<0.001) as compared to controls. FIG. 3B shows mice treated with 10 mg/kg reparixin developing significantly less aneurysms (14% vs 59%, p=0.0163) than PBS: DMSO treated control mice.

FIG. 4A shows representative results from a semi-quantitative array used to evaluate 96 different cytokines in aneurysmal mice. FIG. 4B shows that CXCR1/2 ligand CXCL7 was the primary cytokine increased at two weeks (p=0.028). FIG. 4C shows confirmation data with CXCL7 ELISA.

DETAILED DESCRIPTION

Figure 1A:
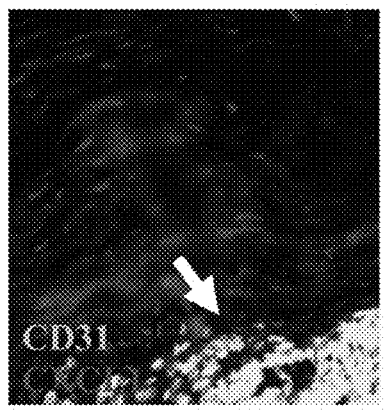
FIGS. 1A and 1B show platelet aggregation and cytokine levels in cerebral aneurysms. Representative immunofluorescence images show CD31+ platelet aggregates in cerebral aneurysms from human and mouse samples; electron microscopy shows platelet aggregates within human tissues. Scalebar=10 μm.
Figure 1A:
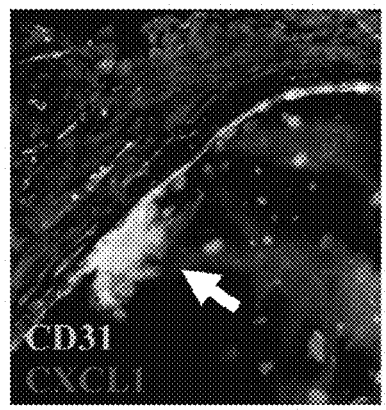
Figure 1A:
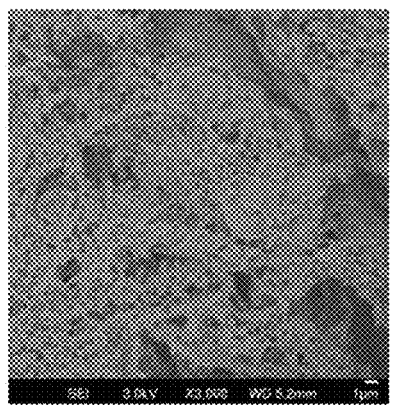

The present disclosure relates to composition and methods useful in connection with use of platelet inhibitors to prevent and/or treat aneurysms.

The present disclosure is based, in part, on the discovery that aneurysm growth relies on platelet aggregation and inflammation pathways, and that the administration of inhibitors of these pathways can reduce and revert the growth of the aneurysm.

For purposes of clarity of disclosure and not by way of limitation, the detailed description is divided into the following subsections:
1. Definitions;
2. Platelet Inhibitors;
3. Methods of Treatment; and
4. Kits.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification can mean "one," but it is also consistent with the meaning of "one or more," "at least one," and "one or more than one."

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of", and "consisting essentially of," the embodiments or elements presented herein, whether explicitly set forth or not.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

An "individual" or "subject" herein is a vertebrate, such as a human or non-human animal, for example, a mammal. Mammals include, but are not limited to, humans, non-human primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

As used herein, the term "disease" refers to any condition or disorder that damages or interferes with the normal function of a cell, tissue, or organ.

An "effective amount" or "therapeutically effective amount" is an amount effective, at dosages and for periods of time necessary, that produces a desired effect, e.g., the desired therapeutic or prophylactic result. In certain embodiments, an effective amount can be formulated and/or administered in a single dose. In certain embodiments, an effective amount can be formulated and/or administered in a plurality of doses, for example, as part of a dosing regimen.

As used herein, the term "derivative" refers to a chemical compound with a similar core structure. For example, trichloromethane (chloroform) is a derivative of methane.

The term "enantiomers" refers to a pair of stereoisomers that are non-superimposable mirror images of each other. A 1:1 mixture of a pair of enantiomers is a "racemic" mixture or a racemate. The term is used to designate a racemic mixture where appropriate.

The term "enantiopure" refers to a sample that within the limits of detection consists of a single enantiomer.

The term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro or levorotatory) in which they rotate plane polarized light at the wavelength of the sodium D line.

The term "isomers" refers to different compounds that have the same molecular formula but differ in arrangement and configuration of the atoms. Also, as used herein, the term "stereoisomer" refers to any of the various stereo isomeric configurations which can exist for a given compound of the presently disclosed subject matter and includes geometric isomers. It is understood that a substituent can be attached at a chiral center of a carbon atom. Also, as used herein, the terms "constitutional isomers" refers to different compounds that have the same numbers of, and types of, atoms but the atoms are connected differently.

"Inhibitors" or "antagonists," as used herein, refer to modulating compounds that reduce, decrease, block, prevent, delay activation, inactivate, desensitize or down-regulate the biological activity and/or expression of a receptor or pathway of interest. The term "antagonist" includes full, partial, and neutral antagonists as well as inverse agonists.

The term "nucleic acid molecule" and "nucleotide sequence," as used herein, refers to a single or double-stranded covalently-linked sequence of nucleotides in which the 3' and 5' ends on each nucleotide are joined by phosphodiester bonds. The nucleic acid molecule can include deoxyribonucleotide bases or ribonucleotide bases, and can be manufactured synthetically in vitro or isolated from natural sources.

The terms "polypeptide," "peptide," "amino acid sequence" and "protein," used interchangeably herein, refer to a molecule formed from the linking of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis or enzymatic synthesis. The terms can apply to amino acid polymers in which one or more amino acid residue is an artificial chemical mimetic of a corresponding naturally occurring amino acid, as well as to naturally occurring amino acid polymers and non-naturally occurring amino acid polymers.

As used herein, the term "disease" refers to any condition or disorder that damages or interferes with the normal function of a cell, tissue, or organ.

As used herein, the term "aneurysm" refers to a bulging, weak area in the wall of a blood vessel. An aneurysm can occur in any blood vessel, but most often develops in an artery rather than a vein. An aneurysm can be categorized by its location, shape, and cause. For example, an aneurysm may be found in many areas of the body, such as brain (cerebral aneurysm), aorta (aortic aneurysm), neck, intestines, kidney, spleen, legs.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing aneurysms, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

2. Platelet Inhibitors

The present disclosure provides platelet inhibitors for use in the methods disclosed herein. A platelet inhibitor can be a molecule, e.g., chemical compound, that inhibits the process of platelet formation. A platelet inhibitor can be a molecule, e.g., chemical compound, that inhibits the process of platelet activation. A platelet inhibitor can be a molecule, e.g., chemical compound, that inhibits thrombus formation. A platelet inhibitor can reversibly or irreversibly inhibit the process involved in platelet activation resulting in decreased tendency of platelets to adhere to one another and to damaged blood vessels' endothelium.

Non-limiting examples of platelet inhibitors for use in the present disclosure include irreversible cyclooxygenase inhibitors (e.g., aspirin), adenosine diphosphate (ADP) receptor inhibitors (e.g., ticlopidine), phosphodiesterase inhibitors (e.g., vorapaxar), inhibitors of glycoprotein (e.g., abciximab), adenosine reuptake inhibitors, thromboxane inhibitors, thromboxane synthase inhibitors, thromboxane receptor antagonists, terutroban, salts thereof, or derivatives thereof. Additional examples of platelet inhibitors for use in the present disclosure include, without any limitation, interfering ribonucleic acids (e.g., siRNA, shRNA), antibodies, aptamers, or peptidomimetics.

In certain embodiments, the platelet inhibitor for use in the present disclosure is an inhibitor of glycoprotein GPIIB/IIIA is a receptor on the platelet surface that undergoes a conformational change upon activation of the platelet allowing it to bind plasma fibrinogen. Because multiple GPIIB/IIIA molecules from different platelets can bind the same fibrinogen molecule, this facilitates platelet aggregation at sites of vascular injury. By preventing the GPIIB/IIIA molecule from interacting with fibrinogen these inhibitors consequently interfere with the process of platelet aggregation.

Non-limiting examples of inhibitors of glycoprotein for use in the present disclosure include abciximab, eptifibatide, tirofiban, lefradafiban, fredabin, lamifiban, clopidogrel, orbofiban, roxifiban, sibrafiban, xemilofiban, ticlopidine, ticagrelor, prasugrel, LM-609, resveratrol, ferric cation, levothyroxine, YM-57029, YM128, a non-peptide mimetic of the tetrapeptide RGDF, a peptide mimetic of the tetrapeptide RGDF, salts thereof, or derivatives thereof. In certain embodiments, the inhibitor of glycoprotein IIB/IIIA is clopidogrel, a salt thereof or a derivative thereof. In certain embodiments, the inhibitor of glycoprotein has the following formula:

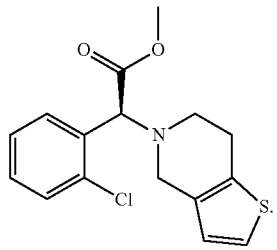 [SMILES: COC(=O)[C@H](c1ccccc1Cl)N1CCc2sccc2C1]

In certain embodiments, the platelet inhibitor for use in the present disclosure inhibits the platelet-driven CXCL7-CXCR1/2 pathway. CXCL7 is a small cytokine belonging to the chemokine family and binds CXCR1 and CXCR2 receptors. CXCL7 exerts its function by activating the CXCR1 and/or CXCR2 and binding sulfated glycosaminoglycans (GAGs) that regulate receptor activity and is released by platelets upon their activation. Upon activation, both CXCR1 and CXCR2 transfer the signal into the cell which results in platelet dysfunction and aneurysm growth. By preventing the interaction of CXCL7 with its receptors and by inhibiting the activity of the CXCR1 and/or CXCR2, these inhibitors consequently interfere with the process of aneurysm development and growth.

In certain embodiments, the platelet inhibitor for use in the present disclosure is an inhibitor of the chemokine (C-X-C motif) ligand 7 (CXCL7). In certain embodiments, the inhibitor of CXCL7 is ethanesulfonic acid. In certain embodiments, the inhibitor of CXCL7 is an antibody anti-CXCL7, or a fragment thereof. In certain embodiments, the antibody can be monoclonal. In certain embodiments, the antibody can be polyclonal. In certain embodiments, the antibody can be humanized. Non-limiting examples of antibodies anti-CXCL7 are disclosed in International Patent Application Nos. PCT/US2011/024123 and PCT/EP2014/060201, which are incorporated herein by reference in their entireties.

In certain embodiments, the platelet inhibitor for use in the present disclosure is an inhibitor of the C-X-C chemokine receptor type 1 (CXCR1). In certain embodiments, the platelet inhibitor for use in the present disclosure is an inhibitor of the C-X-C chemokine receptor type 2 (CXCR2). In certain embodiments, the platelet inhibitor for use in the present disclosure is an inhibitor of CXCR1 and CXCR2. Non-limiting examples of inhibitors of CXCR1 and CXCR2 for use in the present disclosure include SX-682, AZD5069, AZD8797, QBM076, reparixin, SCH-527123, danirixin, navarixin, ladarixin, SB225002, nicotinamide N-oxide, UNBS5162, CXCR2-IN-1, SRT3109, SCH563705, SRT3190, SB265610, elubrixin, SB332235, carydalmine, salts thereof or derivatives thereof. In certain embodiments, the inhibitor of CXCR1 and CXCR2 is reparixin, a salt thereof, or a derivative thereof. In certain embodiments, the inhibitor of CXCR1 and CXCR2 has the following formula:

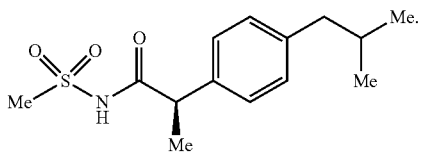 [SMILES: CC(C)Cc1ccc([C@@H](C)C(=O)NS(C)(=O)=O)cc1]

In certain embodiments, the platelet inhibitor for use in the present disclosure is a nucleic acid targeting a protein regulating the platelet-driven CXCL7-CXCR1/2 pathway. In certain embodiments, the nucleic acid targets CXCL7. In certain embodiments, the nucleic acid targets CXCR1 receptor. In certain embodiments, the nucleic acid targets CXCR2 receptor. Non-limiting examples of nucleic acids for use in the present disclosure include siRNAs and shRNAs. siRNA molecules are polynucleotides that are generally about 20 to about 25 nucleotides long and are designed to bind specific RNA sequence (e.g., CXCR1 mRNA or CXCR2 mRNA). siRNAs silence gene expression in a sequence-specific manner, binding to a target RNA (e.g., an RNA having the complementary sequence) and causing the RNA to be degraded by endoribonucleases. siRNA molecules able to inhibit the expression of the CXCR1 or CXCR2 can be produced by suitable methods. There are several algorithms that can be used to design siRNA molecules that bind the sequence of a gene of interest (see e.g., Huesken et al., *Nat. Biotechnol.* 23:995-1001; Jagla et al., *RNA* 11:864-872, 2005; Shabalinea, BMC Bioinformatics 7:65, 2005). Additionally or alternatively, expression vectors expressing siRNA or shRNA can be used (see e.g., Brummelkamp, *Science* 296: 550-553, 2002; Lee et al., *Nature Biotechnol.* 20:500-505, 2002; Elbashir et al., *Nature* 411:494-498, 2001).

In certain embodiments, the platelet inhibitor for use in the present disclosure is a ribozyme that inhibits the expression of CXCR1 and/or CXCR2. Ribozymes are RNA molecules possessing enzymatic activity. One class of ribozymes is capable of repeatedly cleaving other separate RNA molecules into two or more pieces in a nucleotide base sequence specific manner (see Kim et al., *Proc Natl Acad Sci USA*, 84:8788 (1987); Haseloff & Gerlach, *Nature,* 334:585 (1988); and Jefferies et al., *Nucleic Acid Res,* 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, reducing its stability and destroying its ability to directly translate an encoded protein. Methods for selecting a ribozyme target sequence and designing and making ribozymes are generally known in the art.

In certain embodiments, the platelet inhibitor for use in the present disclosure is a gene-editing system that inhibits the expression of CXCR1 and/or CXCR2. Non-limiting examples of gene-editing systems for use in the present disclosure include transcription activator-like effector nucleases (TALENs), zinc-finger nucleases, meganuclease, clustered regularly interspaced short palindromic repeat-associated proteins (CRISPR/Cas9), DNA-repair proteins, DNA-modification proteins, and DNA methyltransferases. Details on the gene-editing systems for use in the present disclosure can be found in Adli et al., *Nat Commun.* 2018 May 15; 9(1):1911 and Maeder & Gersbach, *Mol Ther.* 2016 March; 24(3):430-46, the content of each of which is incorporated by reference in its entirety.

In certain non-limiting embodiments, the present disclosure further provides pharmaceutical formulations of platelet inhibitors for therapeutic use. In certain embodiments, the pharmaceutical formulation includes a platelet inhibitor and a pharmaceutically acceptable carrier. "Pharmaceutically acceptable," as used herein, includes any carrier which does not interfere with the effectiveness of the biological activity of the active ingredients, e.g., platelet inhibitor, and that is not toxic to the patient to whom it is administered. Non-limiting examples of suitable pharmaceutical carriers include phosphate-buffered saline solutions, water, emulsions, such as oil/water emulsions, various types of wetting agents and sterile solutions. Additional non-limiting examples of pharmaceutically acceptable carriers can include gels, bioabsorbable matrix materials, implantation elements containing the inhibitor and/or any other suitable vehicle, delivery or dispensing means or material. Such carriers can be formulated by conventional methods and can be administered to the subject.

In certain embodiments, the pharmaceutical formulations of the present disclosure include stereoisomers, enantiomers, diastereomers, or racemates of the platelet inhibitors. The platelet inhibitors disclosed herein can contain one or more asymmetric centers and can thus give rise to enantiomers, diastereomers, and other stereoisomeric forms that can be defined, in terms of absolute stereochemistry, as (R)- or (S)-. In certain embodiments, the pharmaceutical formulation of the present disclosure includes all possible isomers, including racemic mixtures, optically pure forms, and intermediate mixtures. Optically active (R)- and (S)-isomers can be prepared using chiral synthons or chiral reagents or resolved using conventional techniques. If the platelet inhibitor contains a double bond, the substituent can be E or Z configuration. If the compound contains a disubstituted cycloalkyl, the cycloalkyl substituent can have a cis- or trans-configuration. All tautomeric forms are also intended to be included.

In certain embodiments, the pharmaceutical formulations of the present disclosure can be formulated using pharmaceutically acceptable carriers well known in the art that are suitable for parenteral administration, e.g., intravenous administration, intraarterial administration, intrathecal administration, intranasal administration, intramuscular administration, subcutaneous administration and intracisternal administration. In certain embodiments, the pharmaceutical formulation is formulated for intrathecal administration. For example, but not by way of limitation, the pharmaceutical formulation can be formulated as solutions, suspensions or emulsions.

In certain non-limiting embodiments, the pharmaceutical formulations of the present disclosure can be formulated using pharmaceutically acceptable carriers well known in the art that are suitable for oral administration. Such carriers enable the pharmaceutical compositions to be formulated as tablets, pills, capsules, liquids, gels, syrups, slurries, suspensions and the like, for oral ingestion by a patient to be treated. In certain embodiments, the pharmaceutical formulation can be a solid dosage form.

In certain embodiments, the pharmaceutical formulation can be formulated to release the platelet inhibitor immediately upon administration. Alternatively, the pharmaceutical formulation can be formulated to release the platelet inhibitor at any predetermined time or time period after administration. Such types of compositions are generally known as controlled release formulations, which include (i) formulations that create substantially constant concentrations of the platelet inhibitor within the subject over an extended period of time; (ii) formulations that after a predetermined lag time create substantially constant concentrations of the platelet inhibitor within the subject over an extended period of time; (iii) formulations that sustain the platelet inhibitor's action during a predetermined time period by maintaining a relatively constant, effective level of the platelet inhibitor in the body with concomitant minimization of undesirable side effects; (iv) formulations that localize action of platelet inhibitor, e.g., spatial placement of a controlled release composition adjacent to or in the disease, e.g., endothelial cells, platelet cells; (v) formulations that achieve convenience of dosing, e.g., administering the composition once per week or once every two weeks; and (vi) formulations that target the action of the platelet inhibitor by using carriers or chemical derivatives to deliver the platelet inhibitor to a particular target cell type or a particular target tissue type. In certain embodiments, controlled release is obtained by appropriate selection of various formulation parameters and ingredients, including, e.g., various types of controlled release compositions and coatings. For example, but not by way of limitation, the platelet inhibitor can be formulated with appropriate excipients into a pharmaceutical formulation that, upon administration, releases the platelet inhibitor in a controlled manner, e.g., oil solutions, suspensions, emulsions, microcapsules, molecular complexes, microspheres, nanoparticles, patches and liposomes.

In certain embodiments, the pharmaceutical formulations suitable for use in the present disclosure can include formulations where the platelet inhibitors are contained in a therapeutically effective amount. A "therapeutically effective amount" refers to an amount that is able to prevent and/or reduce the development, growth, and rupture of an aneurysm. The therapeutically effective amount of an active ingredient can vary depending on the active ingredient, e.g., platelet inhibitor, formulation used, the anatomical location of the aneurysm and its severity, and the age, weight, etc., of the subject to be treated. In certain embodiments, a patient can receive a therapeutically effective amount of a platelet inhibitor as a single dose or multiple administrations of two or more doses, which can depend on the dosage and frequency as required and tolerated by the patient. In certain embodiments, the provided methods involve administering the compositions at effective amounts, e.g., therapeutically effective amounts.

3. Methods of Treatment

The present disclosure relates to methods for preventing and/or treating an aneurysm in a subject. The present disclosure provides methods for preventing and/or treating an aneurysm in a subject by inhibiting the platelet activation and aggregation of the subject. As described in detail in the Example section below, the studies presented in the instant application indicate that the inhibition of the CXCL7-CXCR1/2 axis and the inhibition of platelet aggregation can be used to prevent and/or treat aneurysms by inhibiting aneurysm growth and rupture.

Figure 7:
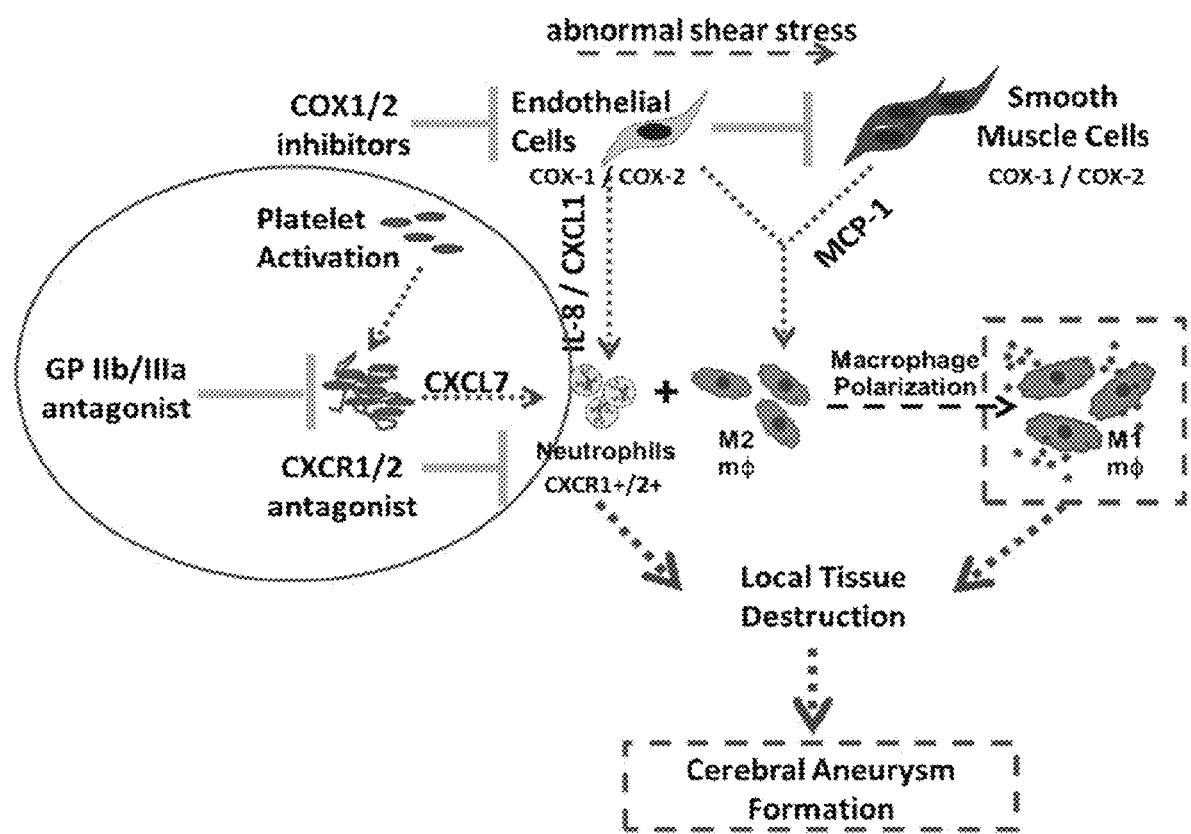
FIG. 7 shows a pathway illustrating the therapeutic role of anti-GPIIb/IIIa and anti-CXCR1/2 anti-platelet therapy in cerebral aneurysm formation.

FIG. 7 illustrates the pathways regulated by the methods disclosed herein. Initially, the dysfunctional endothelium secretes neutrophil chemoattractants such as IL-8/CXCL1. Platelets adhere to damaged endothelium, aggregate and secrete CXCL7 attracting neutrophils via CXCR1/2. The increase in endothelial COX-2 products with co-current decrease in nitric oxide leads to pro-inflammatory smooth muscle cells, which also attracts macrophages via MCP-1. Neutrophils cause a shift in macrophage phenotype from pro-wound healing M2 phenotype towards pro-inflammatory M1 phenotype. This results in local tissue destruction, aneurysm formation, progression, and eventual rupture. The therapy with GPIIb/IIIa antagonists proposed in this grant (blue circle) prevents platelet aggregation, CXCL7 release and neutrophil infiltration. CXCR1/2 antagonists would allow for a more downstream blockade of effects resulting from platelet activation as well as endothelial cell activation.

Aneurysms are excessive localized enlargements of an artery caused by a weakening of the artery wall. The balloon-like bulges have an increased risk of rupture as they increase in size, besides being a potential site for thrombosis and the eventual formation of an embolism. Aneurysms may be the result of a hereditary condition or a later acquired disease. Three particularly lethal types of aneurysms upon rupture are abdominal aortic aneurysm (AAA), thoracic aortic aneurysm (TAA), and cerebral aneurysm (CA).

Aortic aneurysm formation is the result of a thinning medial layer and deterioration of the elastic lamina resulting in weakening of the tensile strength of the arterial wall. Aortic aneurysms are commonly identified in the thoracic and infrarenal aorta, with the latter referred to as abdominal aortic aneurysms (AAA). The pathogenesis of AAA includes endothelial cell (EC) apoptosis, inflammation, and vascular smooth muscle cell (VSMC) proliferation and migration.

Abdominal aortic aneurysm (AAA) is a permanent, localized dilation of the abdominal aorta. It occurs in up to 9% of adults older than 65 years of age, with about 15,000 annual deaths after rupture in the United States (Weintraub L. *N Engl J Med*. (2009) 361: 1114-6). AAA is characterized by a dilatation of all layers of the arterial wall due to elastin loss, smooth muscle cell apoptosis, and compensatory collagen deposition. The hallmarks of AAA include the formation of intraluminal thrombus (ILT), destructive remodeling of structural connective tissue, and chronic adventitial inflammation.

A thoracic aortic aneurysm (TAA) is an aortic aneurysm that presents primarily in the thorax. TAAs, which have an estimated annual incidence of 10.4 per 100,000 people, are typically clinically silent yet potentially fatal, as their natural history is to progressively expand until dissection or rupture occurs (Brownstein et al., *AORTA* (Stamford). 2017; 5(1): 11-20).

Cerebral aneurysms (CA) affect about 5 percent of the population and occur when the wall of a blood vessel in the brain becomes weakened and bulges or balloons out. Pre-rupture treatments are generally limited to surgical clipping or endovascular coiling or a flow diverter can be used to seal off an unruptured brain aneurysm and help prevent a future rupture. However, in some unruptured aneurysms, the known risks of the procedures may outweigh the potential benefit.

Cerebral aneurysms are usually found at the base of the brain just inside the skull, in an area called the subarachnoid space. Rupture of these cerebral aneurysms results in bleeding into the space around the brain and is often referred to as subarachnoid hemorrhage (SAH). This kind of hemorrhage can lead to a stroke, coma and/or death. The present disclosure is based, in part, on the discovery of some mechanisms regulating cerebral aneurysms develop, grow and rupture.

In certain non-limiting embodiments, the present disclosure provides for a method of preventing and/or treating aneurysms in a subject. For example, but not by way of limitation, the present disclosure provides a method for preventing and/or treating a cerebral aneurysm in a subject. In certain embodiments, the method can include administering a therapeutically effective amount of a platelet inhibitor to the subject. In certain embodiments, administration of the platelet inhibitor inhibits the development, growth and/or rupture of an aneurysm in a subject. In certain embodiments, the subject was known to have an aneurysm prior to treatment. In certain non-limiting embodiments, the subject was not known to have an aneurysm prior to treatment.

In certain embodiments, the present disclosure provides methods for reducing the risk of a subject that had an aneurysm from developing new aneurysms, which can include administering a therapeutically effective amount of a platelet inhibitor to the subject.

In certain non-limiting embodiments, the present disclosure provides a method of treating a subject having an aneurysm that includes diagnosing aneurysm in the subject and then treating the subject with a platelet inhibitor. In certain embodiments, the method for diagnosing aneurysms includes performing magnetic resonance imaging (MM) of the brain or abdomen, magnetic resonance angiography (MRA), computed tomography angiography scan (CTA scan), angiogram, or cerebrospinal fluid test. Additional methods for diagnosing aneurysm are disclosed in Calero and Illig, *Semin Vasc Surg*. 2016; 29(1-2):3-17, the contents of which are incorporated by reference herein.

In certain embodiments, the method for diagnosing aneurysms includes determining the levels of a biomarker. In certain embodiments, the biomarker can be a protein (e.g., cytokine) or a nucleic acid isolated from a sample. In certain embodiments, a change in the level and/or presence of the biomarker compared to a reference sample is an indication that the subject has an aneurysm. In certain embodiments, the biomarker is CXCL7. In certain embodiments, the sample can be a blood sample.

As used herein, the term "reference sample" refers to a control for a biomarker that is to be detected in a biological sample of a subject. For example, a control can be the level of a biomarker from a healthy individual without aneurysm. In certain embodiments, a reference sample can be the level of a biomarker detected in a healthy individual that has never had an aneurysm. In certain embodiments, a reference sample can be the level of a biomarker detected in a cohort of healthy individuals that have never had an aneurysm. In certain embodiments, the reference sample can be a predetermined level of a biomarker that indicates presence of an aneurysm in a subject.

In certain embodiments, the protein biomarker is detected using a reagent that specifically binds with the protein (e.g., CXCL7). For example, but without any limitation, the reagent can be an antibody, an antibody derivative, an antigen-binding antibody fragment, and a non-antibody peptide that specifically binds the protein. In certain embodiments, the antibody or antigen-binding antibody fragment is a monoclonal antibody or antigen-binding fragment thereof, or a polyclonal antibody or antigen-binding fragment thereof. In certain embodiments, the protein biomarker can be detected by biophysical platforms such as mass spectrometry.

In certain non-limiting embodiments, the present disclosure provides for a method of preventing the growth and rupture of aneurysms, e.g., cerebral aneurysms, in a subject. In certain embodiments, the method includes administering a therapeutically effective amount of a platelet inhibitor to the subject. In certain embodiments, preventing an aneurysm includes inhibiting and/or preventing the aggregation of platelets in the endothelium of a subject.

Methods disclosed herein can be used for treating any aneurysm. In certain embodiments, methods disclosed herein can be used for treating a cerebral aneurysm, an abdominal aortic aneurysm, a thoracic aortic aneurysm, a saccular aneurysm, a popliteal aortic aneurysm, and an aortic aneurysm. In certain embodiments, methods disclosed herein can be used for treating a cerebral aneurysm. In certain embodiments, the cerebral aneurysm is an intracranial aneurysm. In certain embodiments, the intracranial aneurysm can be saccular, fusiform, dissecting, and micotic type. In certain embodiments, the cerebral aneurysm can be located in the anterior communicating artery, the internal carotid artery, the posterior communicating artery, the ophthalmic artery, the middle cerebral artery, the posterior circulation sites and the basilar artery tip, or their distal segments and/or branches.

In certain embodiments, a platelet inhibitor can be administered to a subject at a dose of about 0.05 mg/kg to about 100 mg/kg. In certain embodiments, a subject can be administered up to about 2,000 mg of the platelet inhibitor in a single dose or as a total daily dose. For example, but not by way of limitation, a subject can be administered up to about 1,950 mg, up to about 1,900 mg, up to about 1,850 mg, up to about 1,800 mg, up to about 1,750 mg, up to about 1,700 mg, up to about 1,650 mg, up to about 1,600 mg, up to about 1,550 mg, up to about 1,500 mg, up to about 1,450 mg, up to about 1,400 mg, up to about 1,350 mg, up to about 1,300 mg, up to about 1,250 mg, up to about 1,200 mg, up to about 1,150 mg, up to about 1,100 mg, up to about 1,050 mg, up to about 1,000 mg, up to about 950 mg, up to about 900 mg, up to about 850 mg, up to about 800 mg, up to about 750 mg, up to about 700 mg, up to about 650 mg, up to about 600 mg, up to about 550 mg, up to about 500 mg, up to about 450 mg, up to about 400 mg, up to about 350 mg, up to about 300 mg, up to about 250 mg, up to about 200 mg, up to about 150 mg, up to about 100 mg, up to about 50 mg or up to about 25 mg of the platelet inhibitor in a single dose or as a total daily dose. In certain embodiments, the subject can be administered from about 50 to about 1,000 mg of the platelet inhibitor in a single dose or a total daily dose. In certain embodiments, a subject can be administered about 1,000 mg of the platelet inhibitor, e.g., clopidogrel, in a single dose or as a total daily dose. In certain embodiments, a subject can be administered about 25 mg or more of the platelet inhibitor, e.g., clopidogrel, in a single dose or as a total daily dose. In certain embodiments, a subject can be administered about 1,000 mg of the platelet inhibitor, e.g., reparixin, in a single dose or as a total daily dose. In certain embodiments, a subject can be administered about 25 mg or more of the platelet inhibitor, e.g., reparixin, in a single dose or as a total daily dose.

It is to be understood that, for any particular subject, specific dosage regimes should be adjusted over time according to the individual need and the professional judgment of the person administering or supervising the administration of the platelet inhibitor. For example, the dosage the platelet inhibitor can be increased if the lower dose does not provide sufficient activity in the treatment of a disease or condition described herein (e.g., cerebral aneurysm). Alternatively, the dosage of the composition can be decreased if the disease (e.g., cerebral aneurysm) is reduced, no longer detectable or eliminated.

In certain embodiments, the platelet inhibitor can be administered once a day, twice a day, once a week, twice a week, three times a week, four times a week, five times a week, six times a week, once every two weeks, once a month, twice a month, once every other month or once every third month. In certain embodiments, the platelet inhibitor can be administered twice a week. In certain embodiments, the platelet inhibitor can be administered once a week. In certain embodiments, the platelet inhibitor can be administered two times a week for about four weeks and then administered once a week for the remaining duration of the treatment. In certain embodiments, a subject can be administered up to about 1,000 mg of the platelet inhibitor in a single dose or as a total daily dose two times a week.

In certain embodiments, the period of treatment can be at least one day, at least one week, at least one month, at least two months, at least three months, at least four months, at least five months or at least six months. In certain embodiments, the platelet inhibitor can be administered until the aneurysm is no longer detectable.

In certain embodiments, the platelet inhibitor can be administered to a subject by any route known in the art. In certain embodiments, the platelet inhibitor can be administered parenterally. In certain embodiments, the platelet inhibitor can be administered orally, intravenously, intraarterially, intrathecally, intranasally, subcutaneously, intramuscularly and rectally. In certain embodiments, the platelet inhibitor can be administered intrathecally. For example, but not by way of limitation, the present disclosure provides methods for the prevention and/or treatment of aneurysm in a subject, e.g., having cerebral aneurysm, by intrathecal administration of a platelet inhibitor.

In certain embodiments, one or more platelet inhibitors can be used alone or in combination with one or more secondary aneurysm inhibitors. For example, but not by way of limitation, methods of the present disclosure can include administering one or more platelet inhibitors and one or more secondary aneurysm inhibitors. "In combination with," as used herein, means that the platelet inhibitor and the one or more secondary aneurysm inhibitors are administered to a subject as part of a treatment regimen or plan. In certain embodiments, being used in combination does not require that the platelet inhibitor and one or more secondary aneurysm inhibitors are physically combined prior to administration, administered by the same route or that they be administered over the same time frame. In certain embodiments, the secondary aneurysm inhibitors is administered before a platelet inhibitor. In certain embodiments, the secondary aneurysm inhibitors is administered after a platelet inhibitor. In certain embodiments, the secondary aneurysm inhibitors is administered simultaneously with a platelet inhibitor.

An "secondary aneurysm inhibitors," as used herein, can be any molecule, compound, chemical or composition that has an anti-aneurysm effect and is provided and/or administered in addition to the platelet inhibitors described herein. Secondary aneurysm inhibitors include, but are not limited to, anti-inflammatory, anti-NF-κB inhibitors, calcium channel blockers, protease inhibitors, metalloproteinase inhibitors, mast cell degranulation inhibitors, free radical scavengers, and mineralocorticoid receptor antagonists. Non-limiting examples of secondary aneurysm inhibitors include simvastatin, pravastatin, pitavastatin, valsartan, candesartan, olemsartan, nifedipine, imidapril, ibudilast, celecoxib, tranilast, fasudil, eplerenone, tetracycline and aspirin. In certain embodiments, the secondary aneurysm inhibitors can be aspirin.

In certain embodiments, administration of the platelet inhibitor to the subject has an anti-aneurysm effect or therapeutic benefit. An "anti-aneurysm effect" or "therapeutic benefit" as used herein, refers to one or more of a reduction in aggregate platelet, a reduction in development of an aneurysm, a reduction of growth of an aneurysm and/or a reduction of rupture of an aneurysm.

4. Kits

The present disclosure provides kits for use in the disclosed methods. In certain embodiments, a kit can include a container that includes a platelet inhibitor or a pharmaceutical formulation thereof. In certain embodiments, the container can include a single dose of the platelet inhibitor or multiple doses of the platelet inhibitor. A container can be any receptacle and closure suitable for storing, shipping, dispensing and/or handling a pharmaceutical product.

In certain embodiments, the kit can further include a second container that includes a solvent, carrier and/or solution for diluting and/or resuspending the platelet inhibitor. For example, but not by way of limitation, the second container can include sterile water.

In certain embodiments, the kits include a sterile container which contains the platelet inhibitor; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the kit can further include instructions for administering the platelet inhibitor. The instructions can include information about the use of the platelet inhibitor for treating the aneurysm. In certain embodiments, the instructions include at least one of the following: description of the platelet inhibitor; dosage schedule and administration for treating the aneurysm; precautions; warnings; indications; counter-indications; over dosage information; adverse reactions; animal pharmacology; clinical studies; and/or references. The instructions can be printed directly on the container (when present), or as a label applied to the container, or as a separate sheet, pamphlet, card, or folder supplied in or with the container. For example, but not by way of limitation, the instructions can describe the method for administration and the dosage amount. In certain embodiments, the instructions indicate that the platelet inhibitor or pharmaceutical formulation thereof can be administered intrathecally. In certain embodiments, the instructions can indicate that the platelet inhibitor or a pharmaceutical formulation thereof can be administered to a subject at a dose of between about 0.05 mg/kg to about 100 mg/kg.

In certain embodiments, the kit can further include a device for administering the platelet inhibitor or a pharmaceutical formulation thereof. For example, but not by way of limitation, the device can include a syringe, catheter, e.g., implantable catheter, and/or pump.

EXAMPLES

The presently disclosed subject matter will be better understood by reference to the following Examples, which are provided as exemplary of the presently disclosed subject matter, and not by way of limitation.

Example 1

One third of patients with subarachnoid hemorrhage have multiple aneurysms. About 20-40% of coiled aneurysms eventually recanalize requiring further surgery. The present example shows that small molecule inhibitors targeting the platelet-driven CXCL7-CXCR1/2 inflammatory pathway can be used to prevent cerebral aneurysm formation and rupture.

Materials and Methods:

Mouse Intracranial Aneurysm Model. Murine intracranial aneurysms were created in female 8-12 week-old C57BL/6 mice (Charles River Laboratories, Wilmington, MA) using a method described previously (Hosaka et al., *Journal of neurointerventional surgery*. 2014; 6:474-9). Briefly, the left common carotid artery and the right renal artery were ligated to induce hypertension. One week later, an Alzet micro-osmotic pump model 1004 (DURECT Corp, Cupertino, CA) was implanted subdermally to deliver Angiotensin II (Bachem AG, Switzerland) at 1000 ng/kg/min. 10 µL of 0.8% porcine elastase (Worthington Biochemical Corp, Lakewood, NJ) in normal saline was injected into the right basal cistern using stereotactic coordinates: 1.2 mm rostral of bregma, 0.7 mm lateral of midline and 5.3 mm ventral of the dorsal aspect of the skull. The animals were fed a hypertensive diet with 8% NaCl and 0.12% BAPN (TEKLAD). Clopidogrel was administered at 1 mg/kg in normal saline via intraperitoneal injection every two days. Reparixin was administered at 10 mg/kg in normal saline via intraperitoneal injection every two days. PBS-treated animals received 10 µL injection of phosphate buffered saline subcutaneously every two days. Control sham-surgery animals represented controls that had the incisions and surgical approach performed but no vessel ligation or intracranial injection.

Human Aneurysm and Artery Specimens. All aneurysm and artery specimens were harvested from living patients at the time of craniotomy and aneurysm clipping surgery. In selected subjects, cerebral aneurysm, superficial temporal artery, and peripheral intravenous blood specimens were collected at the same time. Specimens were immediately placed in RNAlater® stabilization solution (Invitrogen), flash frozen at −20° C., transferred to −80° C. for 24 hours, and then finally stored fresh-frozen in liquid nitrogen.

Cytokine Arrays. Raybiotech cytokine arrays C1000 (Raybiotech, Peachtree Corners, GA) were used to analyze 120 cytokines in aneurysm-induced cerebral vasculature at 2 and 3 weeks (n=3 each) and compared with reparixin-, clopidogrel-treated animals, and with sham surgery animals as controls (n=2). In addition, cytokines were analyzed in in human cerebral aneurysm, superficial temporal artery, and peripheral intravenous blood specimens that were collected at the time of surgery.

Human Aneurysm Specimen Electron Microscopy. Scanning electron microscopy images of human intracranial aneurysm specimens were obtained on JEOL JSM 7800F SEM microscope at 3 kV.

Immunohistochemistry of Mouse and Human Aneurysm Specimens. Murine aneurysm specimens were first fixed in 4% PFA for 24 hours, and then dehydrated in 18% sucrose solution. Tissues were mounted in Tissue-Tek OCT compound (Sakura Finetek USA, Torrance, CA) and sectioned at 5 Heat mediated antigen retrieval in Dako Target Retrieval Solution (Dako, Carpinteria, CA) was performed for all murine immunohistochemistry studies. Following a block in 2% normal horse serum (S-2000, Vector Labs) for 1 hour, the specimens were incubated with rat anti-MECA-32 antibody (BD 550563, BD Biosciences, San Jose, CA) to visualize endothelial cells, rabbit anti-CXCL1/GRO-α antibody (ab86436, Abcam), overnight at 4° C., and washed. For immunohistochemistry of human aneurysm samples, the tissues were fixed in 4% PFA and embedded in paraffin. After tissue sectioning at 5 the samples were de-paraffinized by xylene and ethanol. Heat mediated antigen retrieval in 10 µM Sodium Citrate buffer pH 6.5 for all samples was performed. The staining protocol for CXCL1/GRO-α was then followed exactly as for immunohistochemistry of mouse aneurysm specimens except that mouse anti-human CD31 antibody (IR61061-2, Dako) was used in place of MECA-32 to visualize the endothelial cell layer. The secondary antibodies used were Alexa Fluor 488 donkey anti-rat antibody (A-21208, Life Technologies), Alexa Fluor 488 donkey anti-rabbit antibody (A-21206, Life Technologies), Alexa Fluor 568 donkey anti-rabbit antibody (A-21206, Life Technologies), and Alexa Fluor 594 donkey anti-mouse antibody (A-21203, Life Technologies) and were incubated for 1 hour at room temperature. Finally, for both murine and human specimens, nuclei were counterstained with DAPI (H¬1200, Vector Labs, Burlingame, CA).

In silico Analysis. In silico analysis of cytokine array data was performed using open-source REACTOME data model to evaluate for network of 718 biological interactions. All non-human interactors were converted to their human equivalents. IntAct interactors were included to expand background analysis.

Statistical Analysis. For analysis of Clopidogrel and Reparixin Treatment in Mouse Intracranial Model, it was used Fischer's Exact Test with Boschloo confidence interval method to determine whether aneurysm formation differed between clopidogrel-, reparixin-, and control-treated mice. Each Circle of Willis was examined by a blinded observer and aneurysm formation was recorded (yes/no). P-values<0.05 were defined as statistically significant. For CXCL ELISA test, multiple t-test comparisons with Bonferroni correction were used to determine whether the outcome measure differed across the three types of treatments. P-values<0.05 were defined as statistically significant. P-values<0.1 but >0.5 were defined as marginally significant. For REACTOME analysis, the REACTOME data model was used to evaluate for network of 718 biological interactions. All non-human interactors were converted to their human equivalents. IntAct interactors were included to expand background analysis. Pathways and interactions with p-values<0.01 were considered as marginally significant, <0.0027 as significant (3-sigma), and <0.00006 as highly significant (5-sigma).

Figure 1B:
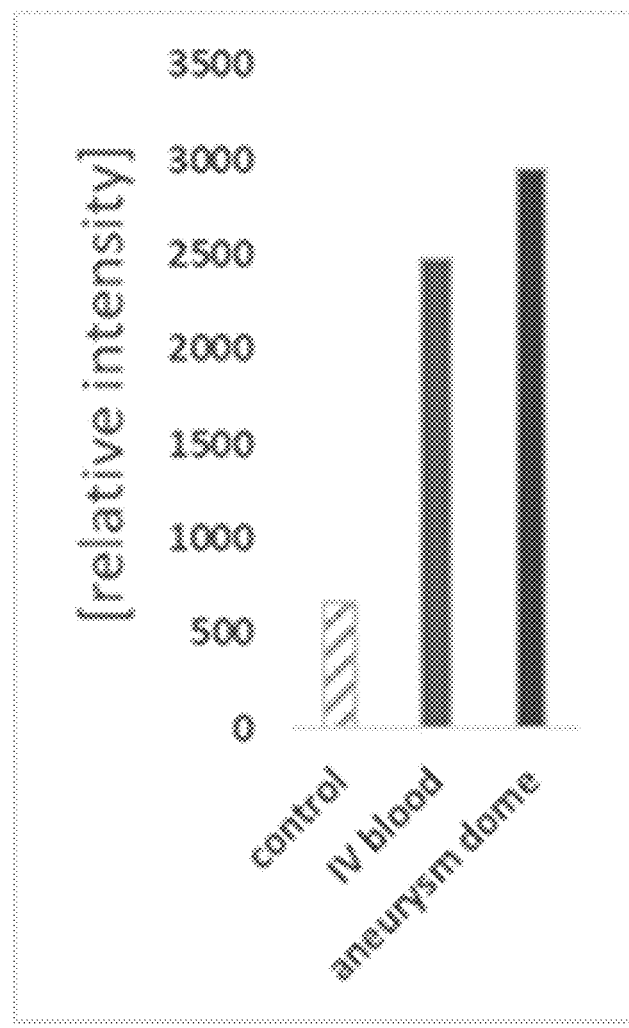
Figures 2A, 2B:
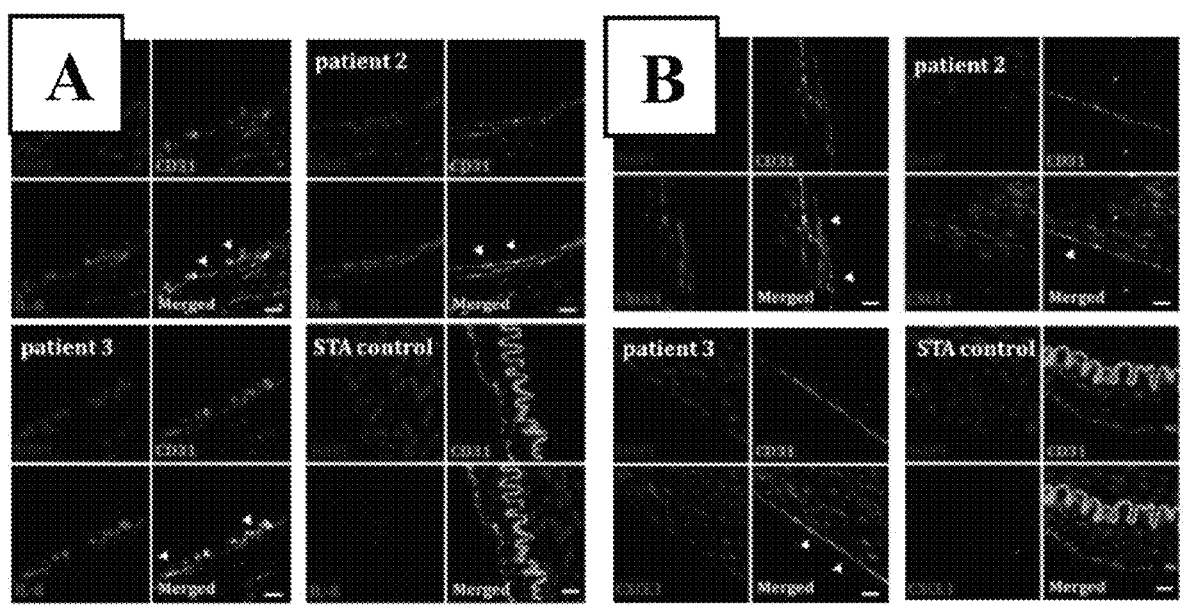
FIGS. 2A-2B show IL8 and GRO-α/CXCL1 in human aneurysms and control arteries.

Results:

Platelets are anuclear cell elements with primary role in hemostasis. When activated, platelets change shape allowing for aggregation and release of pro-inflammatory mediators such as platelet-derived growth factor (PDGF) or C-X-C ligand 7 (CXCL7). Platelets can be activated via TXA2, PGE2 receptors, and other receptors such as GPIIb/IIIa. GPIIb/IIIa is the most abundant integrin present on platelets and its interactions as especially important at moderate-to-low shear stress values, such as the ones found in cerebral aneurysm domes. Human aneurysms domes were analyzed using immunohistochemistry and electron microscopy and showed robust platelet aggregates on the endoluminal surface (FIG. 1A). Surprisingly, as shown in FIG. 1B, analysis of 120 different cytokines collected from patients undergoing cerebral aneurysm clipping surgery showed a robust >3-fold increase in CXCL7 in both peripheral intravenous blood (n=3) and aneurysm dome tissue (n=2) samples when compared to reference control (n=2).

Thrombosis has been shown to promote infiltration of leukocytes into inflamed tissues through a chemotactic gradient mediated by CXCL7 and receptors CXCR1/2. Platelets are also capable of donating glycoprotein IIb/IIIa (GPIIb/IIIa) receptor via microparticles to local neutrophils leading to increased NF-kB activation. This suggests that GPIIb/IIIa and CXCL7 receptors CXCR1/2 could be targeted to prevent platelet and neutrophil induced inflammation. Clopidogrel prevented platelet activation by blocking actions of ADP and preventing conformational change in GPIIb/IIIa receptors. The data disclosed herein show that inhibitors targeting platelet-CXCL7-CXCR1/2 inflammatory axis can be used to prevent murine cerebral aneurysm formation (FIGS. 3A-6).

Figure 6:
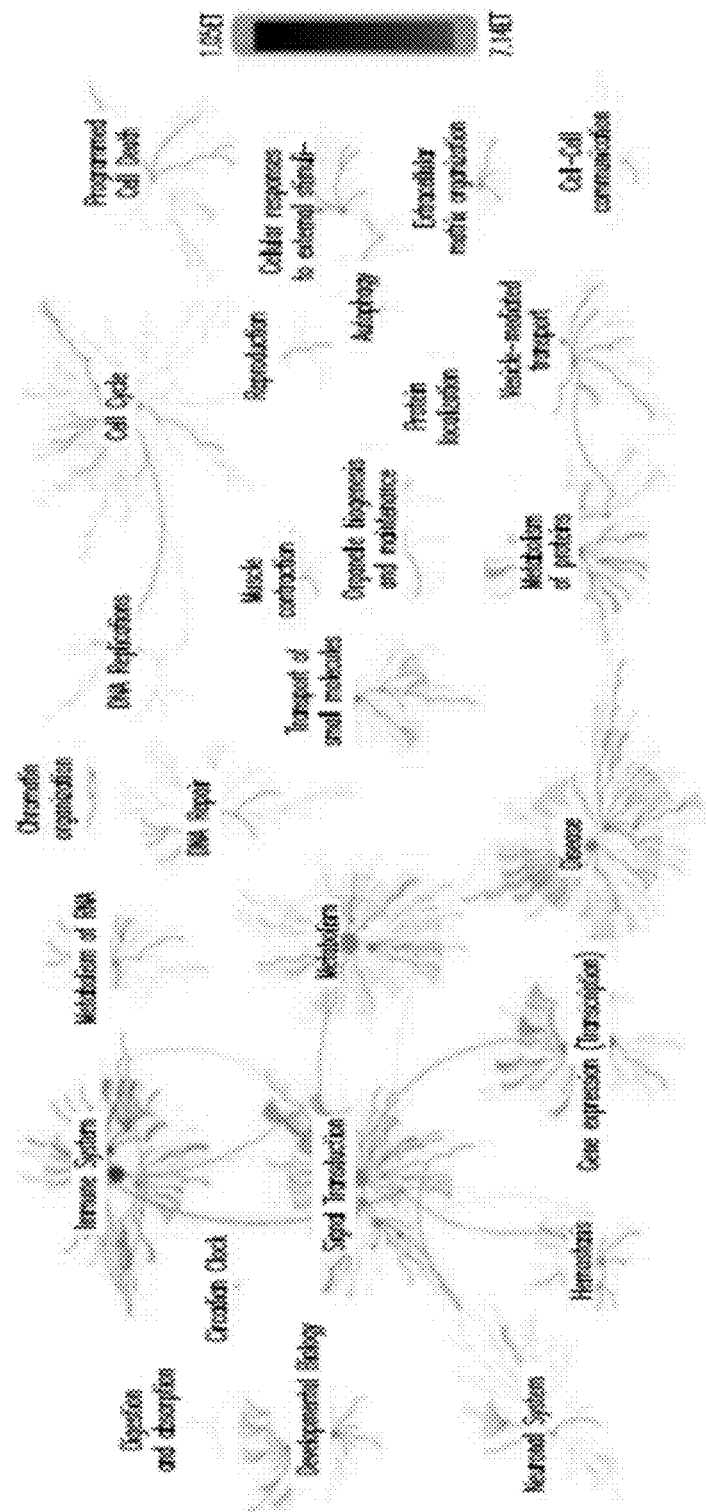
FIG. 6 shows in silico analysis using REACTOME. Pathways with p-values<0.01 were considered as marginally significant, <0.0027 as significant (3-sigma), and <0.00006 as highly significant (5-sigma). Downstream target interactions implicated platelet activation and degranulation, NLRP3 inflammasome, oxidative damage, and interactions with lipid metabolism.

Platelet-neutrophil aggregate formation leads to co-current activation of both of these modulators and increased inflammatory response with extravasation into local vascular environment. These platelet-neutrophil complexes have been found to aggravate atherosclerosis through a positive feedback loop involving CXCL1, CXCR1/2, and CXCL7. The hypothesis that treatment with GPIIb/IIIa antagonists and/or anti-CXCR1/2 receptor blockers could be used to prevent aneurysm formation was tested. Notably, treatment with GPIIb/IIIa antagonists and/or anti-CXCR1/2 receptor blockers decreased platelet aggregation and activation (FIGS. 1, 4A-4C and 5). Further, it was observed a reduction of platelet-induced inflammatory response (FIGS. 3A-6) and of pro-inflammatory M1 macrophage formation (FIG. 6). Furthermore, the treatment prevented inflammation induced by mitochondrial DNA released from damaged and aggregated platelets (FIG. 6). The in silico analysis using REACTOME model implicated platelet activation and degranulation, NLRP-3 inflammasome, oxidative damage, and interactions with lipid metabolism (FIG. 6). Out of 718 pathways and interactions analyzed, 16 were found to be highly significant, 5 were significant, and 4 were marginally significant (FIG. 6 and Table 1).

TABLE 1

| PATHWAY NAME | p VALUE |
|---|---|
| Chemokine receptors | 1.11E−16 |
| IL-10 | 1.11E−16 |
| IL-4 and IL-13 | 1.11E−16 |
| Signaling by interleukins | 1.11E−16 |
| Cytokine signaling | 1.11E−16 |
| Peptide-ligand Binding receptors | 6.37E−13 |
| Immune system | 4.19E−10 |

TABLE 1-continued

| PATHWAY NAME | p VALUE |
|---|---|
| VEGF | 3.69E−07 |
| MMP Activation | 4.72E−07 |
| TNF pathway | 1.39E−06 |
| TNFR2 non-canonical NF-kb pathway | 1.03E−04 |
| RUNX1, FOXP3 and Tregs | 1.25E−05 |
| collagen degradation | 9.42E−05 |
| ECM degradation | 2.77E−04 |
| platelet degranulation | 2.87E−04 |
| platelet activation | 0.002 |
| SASP phenotype | 0.002 |
| NLRP3 inflammasome | 0.003 |

As described above, activated platelets can release pro-inflammatory microparticles and components of mitochondria, which then in turn can act as pro-inflammatory mediators themselves. The NLRP-3 inflammasome activation has direct effects on mitochondrial function and metabolism. Signaling via NLRP3 primary product IL-1 can lead to metabolic dysregulation and autoinflammation. Therefore, inhibitors targeting platelet-derived CXCL7-CXCR1/2 inflammatory axis prevent cerebral aneurysm formation.

These data show that platelet aggregation and inflammation is intimately involved with the process of aneurysm growth. Specifically, inhibitors targeting platelet-CXCL7-CXCR1/2 inflammatory axis can be used to prevent murine cerebral aneurysm formation. In silico analysis of targeted therapy against CXCL7-CXCR1/2 platelet inflammatory axis across 718 pathways using REACTOME model implicated platelet activation and degranulation, NLRP-3 inflammasome, oxidative damage, and interactions with lipid metabolism (FIG. 7).

Figures 3A, 3B:
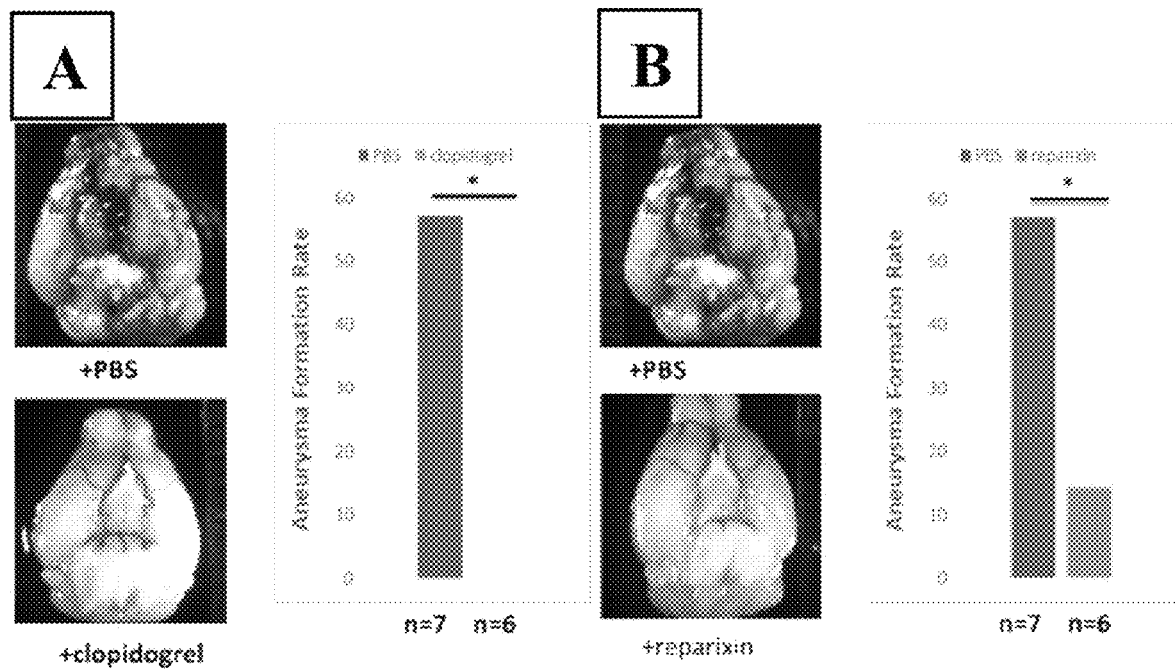
FIGS. 3A-3B show platelet blockade in mouse cerebral aneurysm model.
Figures 4A, 4B:
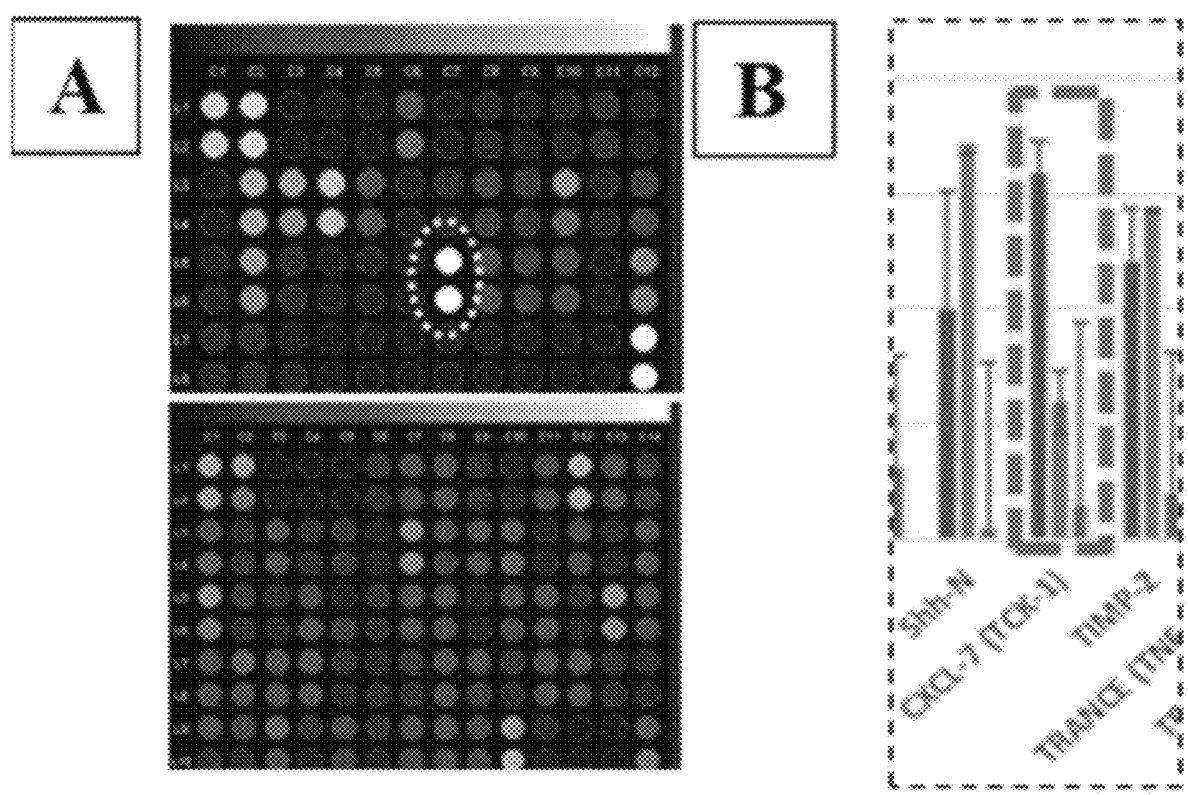
FIGS. 4A-4C show analysis of 96 different cytokines implicating CXCL7 in platelet inflammatory pathway.
Figure 4C:
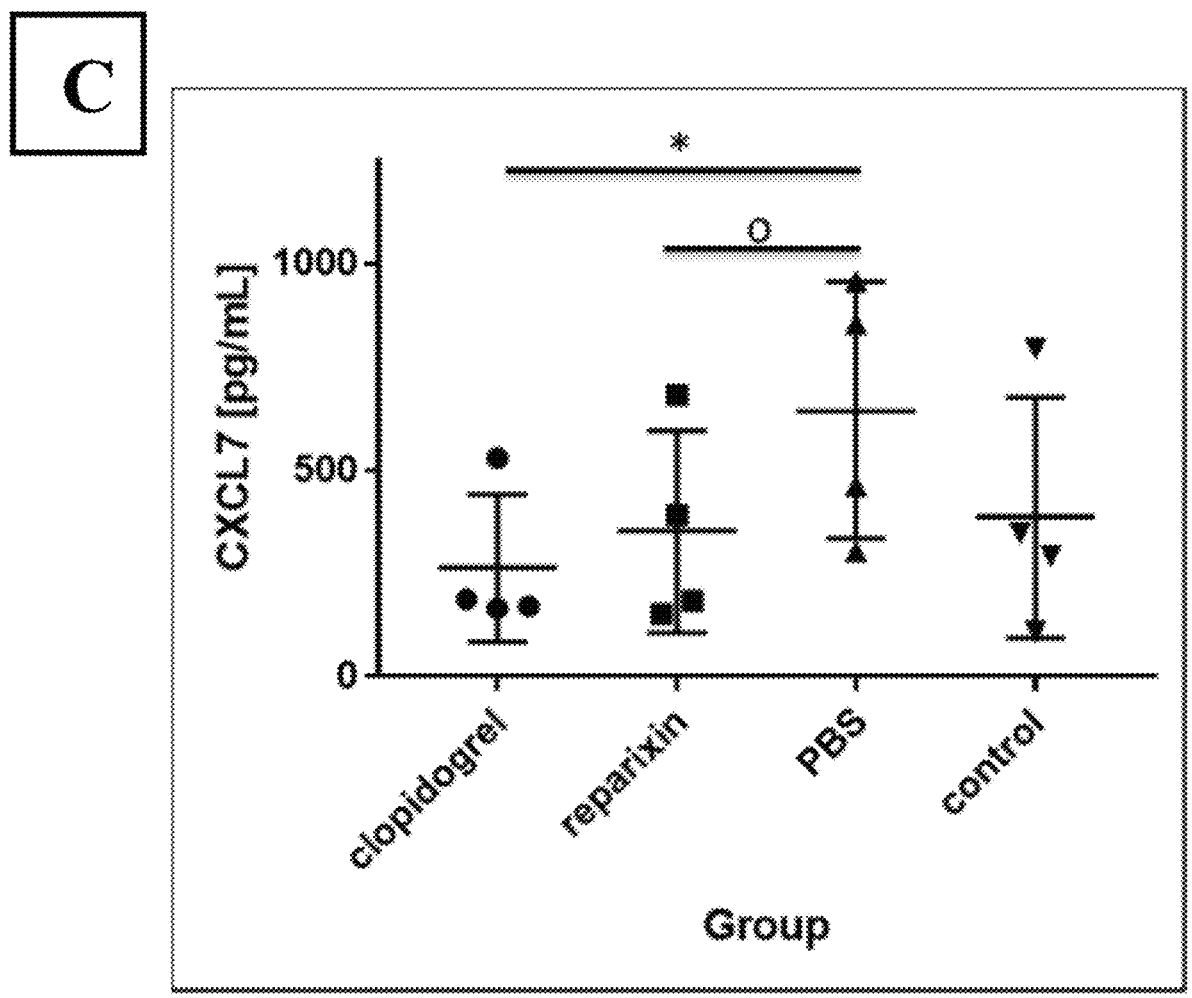
Figure 5:
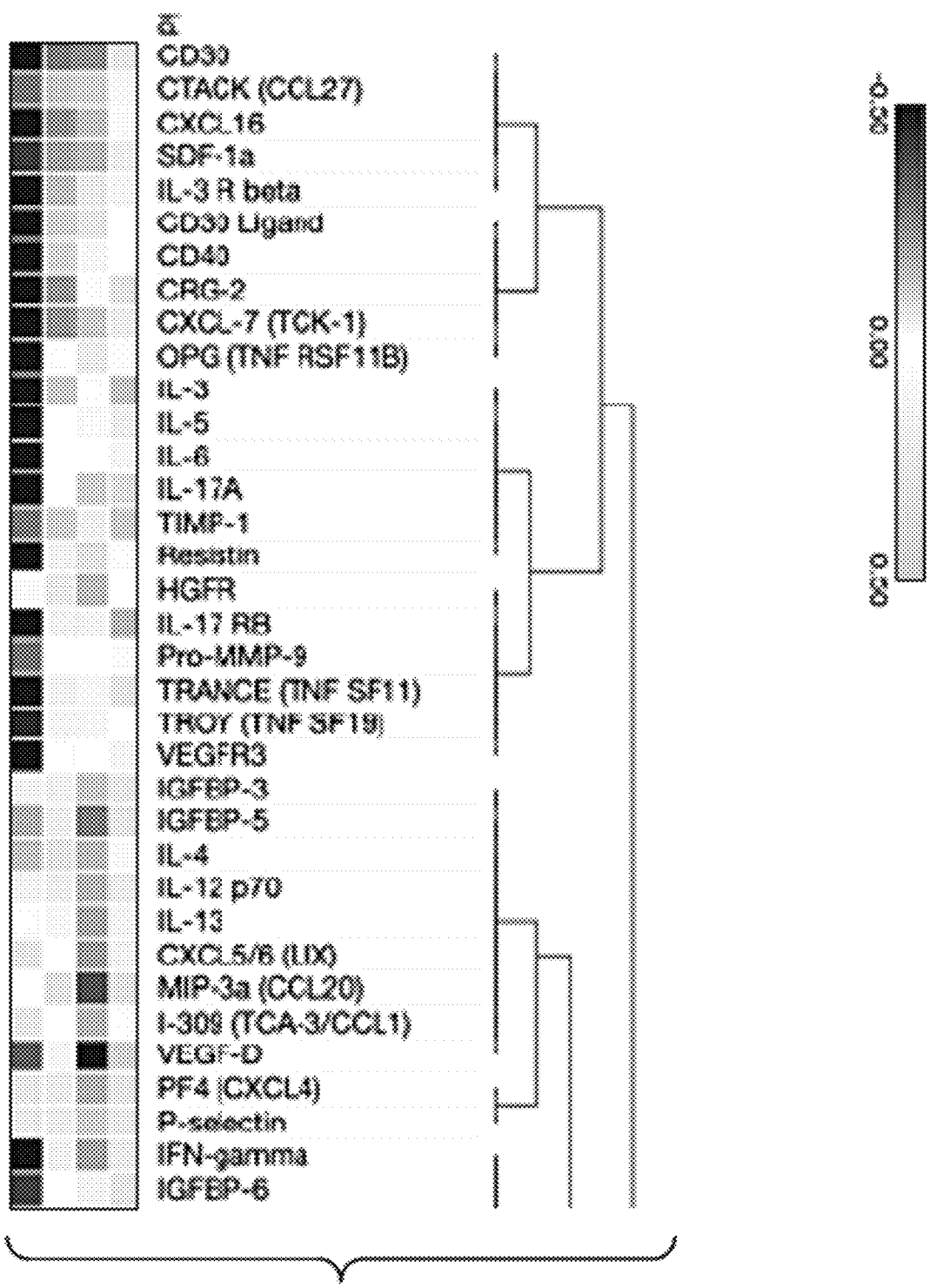
FIG. 5 shows temporal dynamics of 96 cytokines indicating that antiplatelet blockade significantly attenuates the inflammatory profile. Analysis showed variable profile at 2 versus 3 weeks in aneurysmal mice. Clopidogrel had a moderate response while anti-CXCR1/2 blockade (reparixin) showed robust anti-inflammatory effects.
Figure 5:
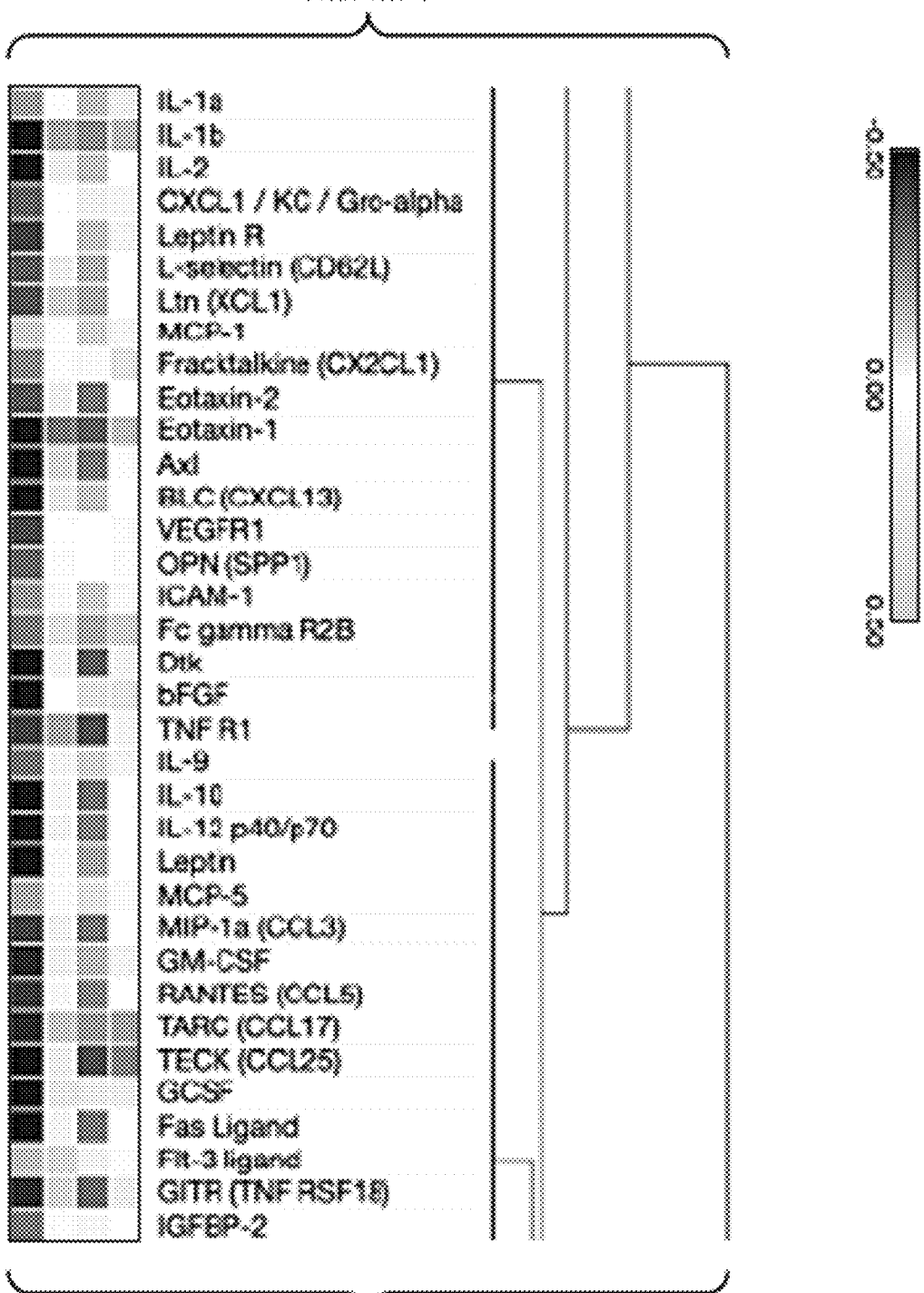
Figure 5:
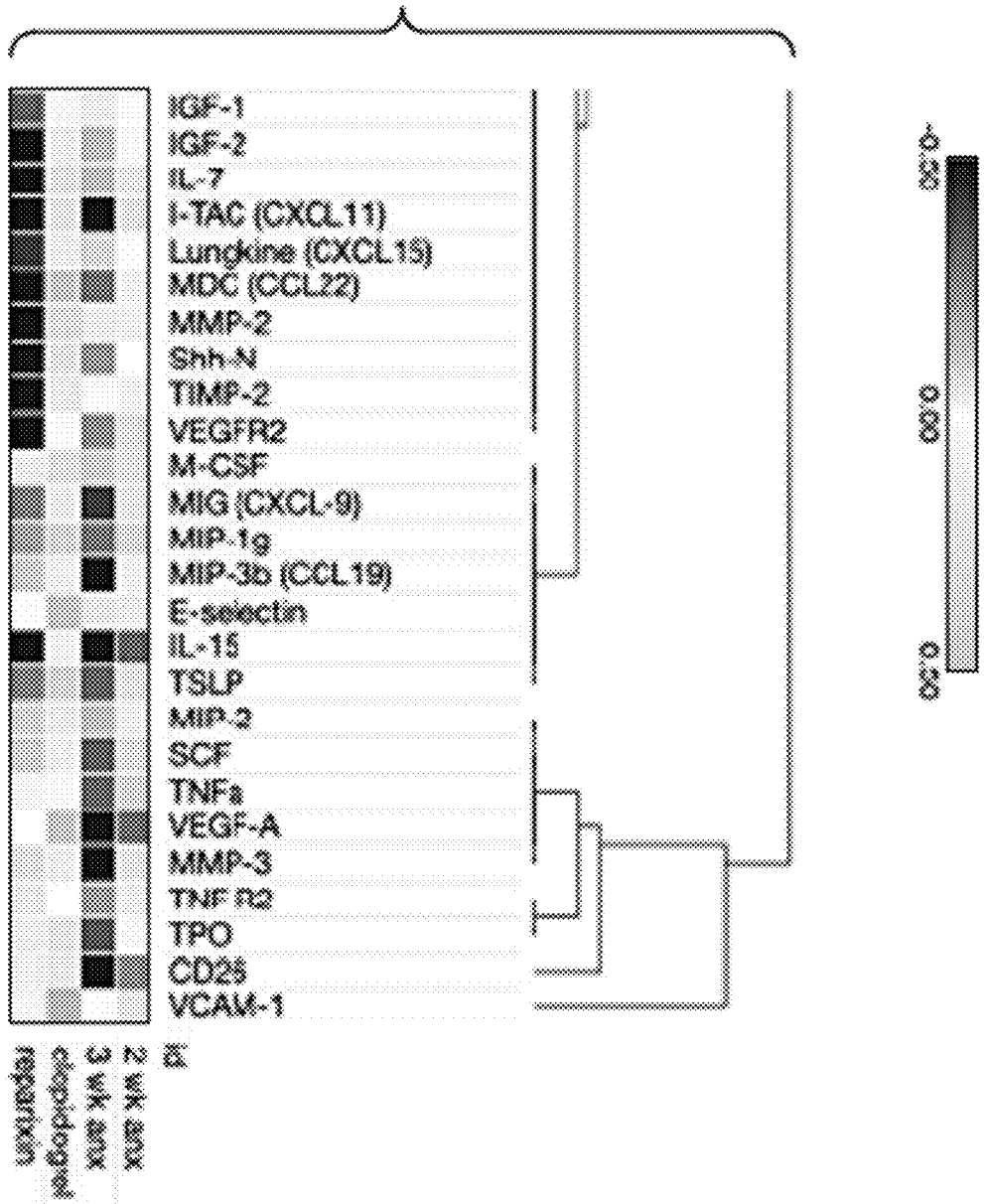

Reparixin, an anti-CXCR1/2 antagonist is currently in phase III clinical trials for efficacy in several malignancies. Therefore, there exists a real possibility to attenuate further aneurysm growth with these agents (FIGS. 3A, 3B and 4C). Notably, the platelet derived CXCL7-CXCR1/2 pathway has never been described or implicated in cerebral aneurysm formation.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method of clinically treating a subject with a cerebral aneurysm, comprising administering to the subject a therapeutically effective amount of a targeted platelet inhibitor selected from the group consisting of clopidogrel, reparixin, and a combination thereof, wherein the targeted platelet inhibitor is administered to the subject at least once a day and for at least one week.

2. The method of claim 1, further comprising administering a therapeutically effective amount of a secondary aneurysm inhibitor.

3. The method of claim 1, wherein the platelet inhibitor is administered to the subject at a dose from about 0.05 mg/kg to about 100 mg/kg.

4. The method of claim 1, wherein administration of the platelet inhibitor reduces the development, growth and/or rupture of the aneurysm.

5. A method of clinically preventing or reducing the risk of growth and/or rupture of a cerebral aneurysm in a subject in need thereof, comprising administering to the subject a therapeutically effective amount of a targeted platelet inhibitor selected from the group consisting of clopidogrel, reparixin, and a combination thereof, wherein the targeted platelet inhibitor is administered to the subject at least once a day and for at least one week.

6. The method of claim 5, further comprising administering a therapeutically effective amount of a secondary aneurysm inhibitor.

7. The method of claim 5, wherein the platelet inhibitor is administered to the subject at a dose from about 0.05 mg/kg to about 100 mg/kg.

8. The method of claim 5, wherein administration of the platelet inhibitor reduces the development, growth and/or rupture of the aneurysm.

\* \* \* \* \*